(12) United States Patent
Dahl et al.

(10) Patent No.: US 10,011,548 B2
(45) Date of Patent: Jul. 3, 2018

(54) PROCESS FOR PRODUCTION OF DME FROM CRUDE METHANOL

(71) Applicant: Haldor Topsøe A/S, Kgs. Lyngby (DK)

(72) Inventors: Per Juul Dahl, Vedbæk (DK); Janni Østergaard, Brønshøj (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/422,433

(22) PCT Filed: Aug. 14, 2013

(86) PCT No.: PCT/EP2013/066977
§ 371 (c)(1),
(2) Date: Feb. 19, 2015

(87) PCT Pub. No.: WO2014/029672
PCT Pub. Date: Feb. 27, 2014

(65) Prior Publication Data
US 2015/0239813 A1   Aug. 27, 2015

(30) Foreign Application Priority Data

Aug. 21, 2012   (WO) ............... PCT/EP2012/066253

(51) Int. Cl.
*C07C 41/42* (2006.01)
*B01D 3/14* (2006.01)
*C07C 41/09* (2006.01)
*B01J 19/24* (2006.01)

(52) U.S. Cl.
CPC ............. *C07C 41/42* (2013.01); *B01D 3/143* (2013.01); *B01J 19/24* (2013.01); *C07C 41/09* (2013.01); *B01J 2219/00006* (2013.01); *B01J 2219/24* (2013.01)

(58) Field of Classification Search
USPC .................. 568/618, 698, 471, 472
See application file for complete search history.

(56) References Cited

U.S. PATENT DOCUMENTS

2011/0065963 A1 * 3/2011 Guo ............... B01J 29/005
568/698

FOREIGN PATENT DOCUMENTS

EP   0 124 078 A1   11/1984

* cited by examiner

*Primary Examiner* — Pancham Bakshi
(74) *Attorney, Agent, or Firm* — Blank Rome LLP

(57) ABSTRACT

The invention provides a process for the production of purified dimethylether (DME). Methanol is dehydrated to provide a first DME-containing product. The first DME-containing product is purified in a two-stage process. The invention also provides an apparatus arranged to carry out said process.

5 Claims, 3 Drawing Sheets

US 10,011,548 B2

PROCESS FOR PRODUCTION OF DME FROM CRUDE METHANOL

FIELD OF THE INVENTION

The invention relates to processes for the production of purified dimethylether (DME). Methanol is dehydrated to provide a first DME-containing product. The first DME-containing product is purified in a two-stage process. The invention also relates to an apparatus arranged to carry out said process.

BACKGROUND TO THE INVENTION

The production of high-purity dimethyl ether (DME) is a commercially-important process. Typically, DME is formed by dehydration of methanol (MeOH) in a DME reactor system.

The feed to a DME reactor system is methanol, which usually contains a certain amount of water and other impurities (e.g. other organic alcohols, ketones, etc.). Water is an undesirable inhibitor of the dehydration to DME.

The DME obtained from a DME reactor system is typically in vapour form, and also contains unreacted methanol, water, and impurities (both those which were present in the methanol feed and those generated by the DME reactor system itself).

The vaporous DME is cooled and then subjected to column distillation, which provides an offgas stream of light fractions (e.g. $CH_4$, $CO_2$, $N_2$), DME product and a stream containing unreacted MeOH and water. Unreacted MeOH and water are recycled, the water is separated, and the methanol re-enters the system after purification.

Through such methods, a purity of over 99% DME can be obtained. However, for certain purposes (e.g. medicinal uses or personal care), extremely high purity (>99%) is required. The higher the initial purity of the DME, the more difficult it proves to obtain even a small increase in purity. This difficulty is further compounded by the presence of the impurities—especially the light fractions—and the liquid-vapour equilibrium constant of DME.

JP 2005-298457 discloses a method for producing DME in which methanol is obtained from synthesis gas.

U.S. Pat. No. 6,548,856 discloses a separation process for one-step production of DME from synthesis gas.

U.S. Pat. No. 5,750,799 discloses a process for the production of DME and recovery from methanol.

Other patent documents in the field of DME production and purification include U.S. Pat. No. 4,560,807, U.S. Pat. No. 5,684,213, DE 42 22 655, JP 2004-091327 and CN 1377871.

US 2011/0065963 discloses one process for providing high purity DME. The process involves a gas/liquid separator, in combination with an absorption column, receiving absorption liquid comprising water and methanol from a DME rectifier.

There remains a need for a process and apparatus which can provide DME with improved purity and efficiency over the processes of the prior art.

SUMMARY OF THE INVENTION

In summary, the invention provides a process for the production of dimethylether (DME), said process comprising the steps of:

a. dehydrating a methanol stream in the presence of a catalyst in a DME reactor system to provide a first DME-containing product;
a. introducing the first DME-containing product into an olefin stripper column, in which it is separated into
   i. olefin stripper light fractions, and
   ii. a second DME-containing product;
b. introducing the second DME-containing product into a DME column, in which it is separated into
   i. DME column light fractions,
   ii. purified DME and
   iii. unreacted methanol and water The effect of using a configuration with an olefin stripper with a reflux liquid comprising DME is that a higher purity DME product is obtained.

In a further embodiment the olefin stripper light fractions is cooled and in a gas/liquid separator is separated into a gas fraction and a reflux liquid, and the reflux liquid is used as reflux liquid in the olefin stripper, with the associated benefit of providing a volume of reflux liquid comprising DME which will be purified.

In a further embodiment the sensible heat of the first DME containing product provides energy for the olefin stripper column; i.e. no re-boiler is required.

In a further embodiment the unreacted methanol and water are fed back into step a, with the associated benefit of providing efficient use of reagents.

In a further embodiment one or more of the light fractions are separated into DME-containing off-gases, said off-gases are combined, washed with methanol to extract DME and the DME-containing methanol recycled to the methanol stream inputted to step a with the associated benefit of providing efficient use of reagents.

In a further embodiment said methanol stream of step a is obtained by passing a feed of crude methanol through a combined stabiliser/waste water column, with the associated benefit of obtaining a product of increased purity.

In a further embodiment heat from step a. is used to heat the combined stabiliser/waste water column, with the associated benefit of increasing the energy efficiency of the process.

The invention also provides an apparatus (100) for the production of dimethylether, said apparatus comprising:

a. a DME reactor system (110), arranged so as to provide a first DME-containing product (111) from a methanol stream (93) in the presence of a catalyst;
b. an olefin stripper column (120) connected to the DME reactor system (110) and arranged to receive the first DME-containing product (111) from said DME reactor system (110), and which is arranged so as to separate the first DME-containing product (111) into
   i. olefin stripper light fractions (121), and
   ii. a second DME-containing product (122);
c. a DME column (130) connected to the olefin stripper column (120) and arranged to receive the second DME-containing product (122) from said olefin stripper column (120), said DME column (130) arranged so as to separate the second DME-containing product (122) into
   i. DME column light fractions (131),
   ii. purified dimethylether (132) and
   iii. unreacted methanol and water (133).

This apparatus has the associated benefit of being efficient for purification of DME.

In a further embodiment the apparatus further comprises a means for cooling and a gas/liquid separator, wherein the means for cooling is arranged for receiving said olefin stripper light fractions and directing the cooled olefin stripper light fractions to a gas/liquid separator, and wherein the gas/liquid separator and olefin stripper column are further arranged for directing the separated liquid as reflux liquid in the olefin stripper column.

In a further embodiment the apparatus further comprises a combined stabiliser/waste water column (90) arranged upstream the DME reactor system (110), and arranged so as to provide said purified methanol stream (93) from a feed of crude methanol (81), with the associated benefit of providing a high purity DME product by reducing the amount of impurities from methanolfeed.

In a further embodiment the combined stabiliser/waste water column (90) is arranged for receiving the unreacted methanol and water from the DME column (130), with the associated benefit of providing efficient use of the raw materials.

In a further embodiment the apparatus further comprises a methanol wash column (140), arranged so as to receive DME-containing off-gases (123, 133) from said olefin stripper column (120) and said DME column (130), wash them with methanol to extract DME and then pass the resulting DME-containing methanol to the methanol stream (93) inputted to step a, with the associated benefit improved DME recovery and reduced waste of methanol.

Further details of the invention will become apparent from the following detailed description, the examples and the appended claims.

DETAILED DESCRIPTION OF THE INVENTION

The invention will now be described in more detail with reference to the Figures.

Figure 1:
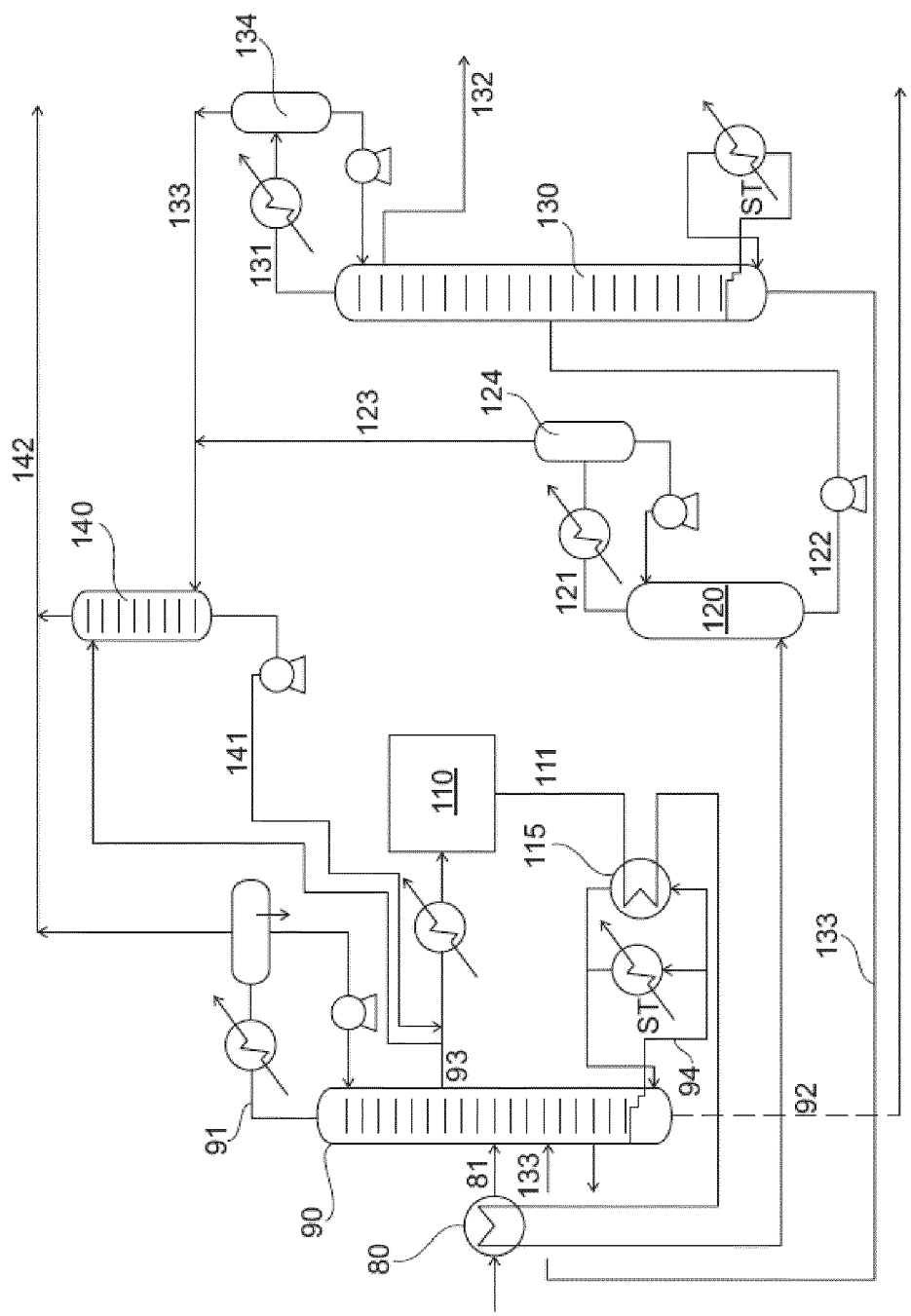
FIG. 1 shows a schematic flow-diagram representing the method and apparatus of the invention.

FIG. 1 shows a flow-diagram representing the method and apparatus of the invention. The term "ST" indicates a steam input.

A feed 81 of crude methanol (MeOH) neutralised with caustic is fed to a combined stabiliser/waste water column 90. This column is also fed with the effluent (mainly unreacted methanol and water 133) from the downstream DME column 130. Impurities in the crude MeOH in the form of light components 91 will leave via the top of the stabiliser column 90. Heavy components 92 and 94 will leave through the bottom of the stabiliser column 90, partly together with water.

A purified methanol stream 93 is drawn from the stabiliser column 90, typically between 3-7 stages, more typically 5 stages above the feed stage. The purified methanol stream 93 can be used as feed to the DME reactor(s). The water content of this purified methanol stream 93 can be adjusted to be less than—or the same as—that in the incoming crude methanol feed 81.

The methanol stream 93 is dehydrated in the presence of a catalyst in a DME reactor system 110 to provide a first DME-containing product 111 (step a.). The DME reactor system is described in more detail in relation to FIGS. 2 and 3, below.

In step b. the first DME-containing product 111 is then introduced into an olefin stripper column 120, in which it is separated into
i. light fractions 121, and
ii. a second DME-containing product 122.

Light fractions 121 (which comprise inter alia methane, $CO_2$ and $N_2$) are withdrawn from the top of said olefin stripper column, while a second DME-containing product 122 is withdrawn from the bottom of said olefin stripper column 120.

In step c., the second DME-containing product 122 is then introduced into a DME column 130, in which it is separated into
i. light fractions 131,
ii. purified DME 132 and
iii. unreacted methanol and water 133.

As for the olefin stripper column 120, any light fractions 131 remaining in the second DME-containing product 121 are withdrawn from the top of said DME column 130. Purified DME 132 is removed 0 to 6 stages from the top of the DME column 130. Unreacted methanol and water 133 are removed from the bottom of the DME column, and suitably fed back into the combined stabiliser/waste water column 90.

Suitably all steps of the invention a. b. and c. are carried out in direct series; i.e. without any intervening steps.

Usually, a water cooler is present between the DME reactor system 110 and the DME column 130, so as to reduce the temperature of the first DME containing product 111 to a temperature between 80 and 100 suitable for fractionation in the DME column 130. However, by introducing an olefin stripper column 120 into the apparatus 100, and using sensible heat in stream 111 to heat the olefin stripper column 120, improved purification of the DME can be carried out, without a re-boiler.

Figure 2:
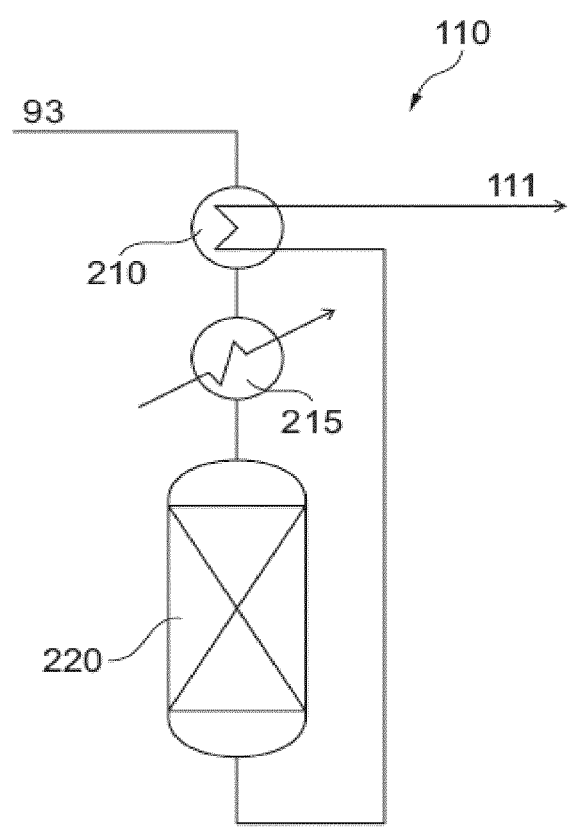
FIGS. 2 and 3 show options for the internal components of two possible DME reactor systems

FIG. 2 shows a standard set-up for a DME reactor system 110. Methanol stream 93 is passed through a heat exchanger 210, in which it is heated by heat exchange with the first DME-containing product stream 111. Before the methanol stream 93 is passed to an adiabatic DME reactor 220, a start-up heater 215 is present to regulate the temperature of said methanol stream 93, and to avoid large temperature swings in the DME reactor system 110. The methanol stream 93 is sent to the DME reactor system 110 at a temperature of between 150 and 180° C., and a pressure of between 15 and 25 bar.

In the adiabatic DME reactor 220, the methanol stream 93 is passed over a catalyst, which converts it to DME. Suitable catalysts for the conversion of methanol to DME may be naturally-occurring or synthetic, and include zeolites, alumina, silica-alumina, metal catalysts (e.g. copper), and combinations thereof.

Figure 3:
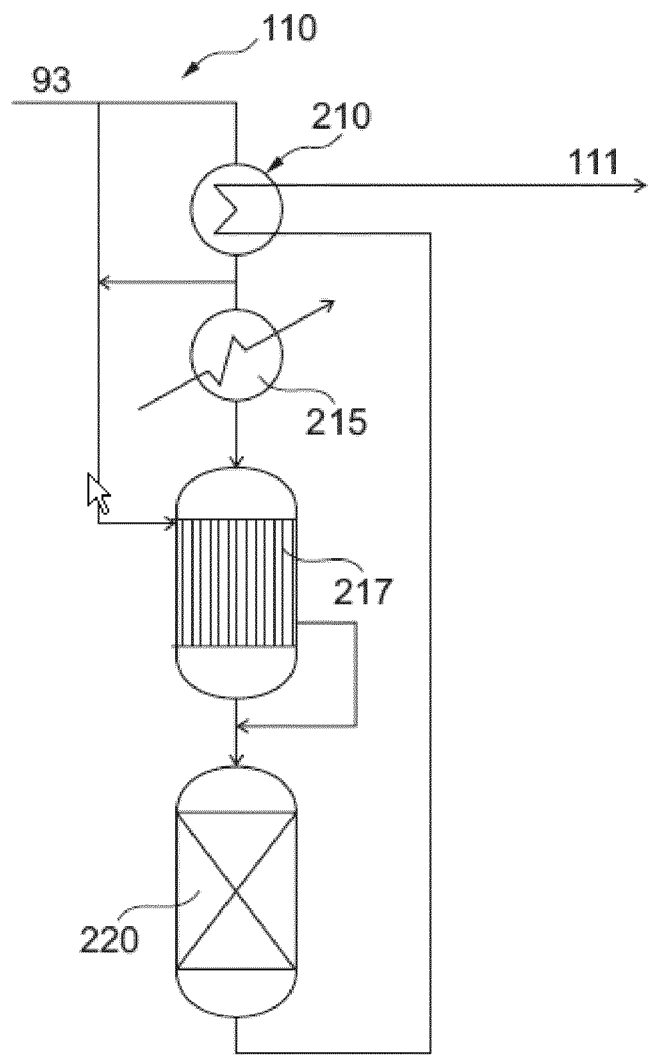

FIG. 3 shows a set-up similar to that of FIG. 2, comprising a heat exchanger 210 a start-up heater 215 and an adiabatic DME reactor 220. In addition, the set-up in FIG. 3 comprises a heat-exchange DME reactor 217, as described in co-pending application WO2011/0952270. The methanol stream 93 is split prior to the heat exchanger 210, and is used as a heat-sink for the heat-exchange DME reactor 217. The set-up of FIG. 3 allows a higher operation temperature of the DME reactors 217 and 220, making this process more efficient.

Additional details of the DME reactor system and components thereof are known to the person skilled in the art, and may e.g. be obtained from U.S. Pat. No. 5,684,213 and U.S. Pat. No. 4,560,807, which are hereby incorporated by reference.

Light fractions 121 and 131 from the olefin stripper column 120 and the DME column 130, respectively are individually separated into off-gas streams 123, 133 in column overhead separators 124, 134. These off-gas streams 123, 133 usually contain residual DME. To isolate this DME, the two off-gas streams 123, 133 are combined and washed with methanol (from methanol stream 93) in a methanol wash column 140. Methanol containing DME 141 is then re-introduced to the methanol stream 93, while combined off-gas 142 is separated. DME in the recycled stream 141 passes unaffected through the DME reactor system 110.

The invention also provides an apparatus (100) for the production of dimethylether. The apparatus comprises:
a. a DME reactor system (110), arranged so as to provide a first DME-containing product (111) from a methanol stream (93) in the presence of a catalyst;
b. an olefin stripper column (120) connected to the DME reactor system (110) and arranged to receive the first DME-containing product (111) from said DME reactor system (110), and which is arranged so as to separate the first DME-containing product (111) into
   i. light fractions (121), and
   ii. a second DME-containing product (122);
c. a DME column (130) connected to the olefin stripper column (120) and arranged to receive the second DME-containing product (122) from said olefin stripper column (120), said DME column (130) arranged so as to separate the second DME-containing product (122) into
   i. light fractions (131),
   ii. purified dimethylether (132) and
   iii. unreacted methanol and water (133).

Suitably, in the apparatus of the invention, a re-boiler is not present between the DME reactor system and the DME column. Instead, heat sensible heat in the stream from the DME reactor is used to heat the olefin stripper column 120, allowing improved purification of the DME to be carried out, without a re-boiler.

All features of the process of the invention described above are also relevant to the apparatus of the invention.

Other advantages of the invention include:
- the combination of feed preparation column and waste water column saves on number of equipment and on energy consumption
- Feedstock impurities are removed resulting in more pure DME product
- Less water is introduced to the DME reactor resulting in a smaller reactor
- Less impurities in the feed to DME reactor increases catalyst activity and prolongs catalyst life time
- Efficient heat integration, minimizing the production cost and at the same time ensuring full individual control of all the columns and reactors The invention has been described with reference to a number of embodiments in the figures and examples. However, the invention should not be considered as strictly limited thereto. The skilled person may perform variations of the invention by e.g. combining features and elements from various embodiments, while remaining within the scope of the claimed invention.

EXAMPLES

Calculations were made to determine the effect of the olefin stripper section.

Table 1 shows data for a DME layout with no olefin stripper section and table 2 shows the same data with an olefin stripper section. It appears that the purity of the DME product has improved from 99.84 to 99.97 for the cost of an additional steam consumption of 9% or 1% on total energy consumption. Furthermore it shows that the level of impurities and water content is lower in the inlet reactor than in the feed MeOH

TABLE 1

| Component | Feed MeOH (81) | Reactor feed (93) | Purified DME product (132) | MeOH/H$_2$O Recycle (133) | H$_2$O Effluent | Steam consumption |
|---|---|---|---|---|---|---|
| | | | Flow rate | | | |
| | 37.379 kg/h [wt %] | 43.977 kg/h [wt %] | 24.585 kg/h [wt %] | 19.268 kg/h [wt %] | 12.583 kg/h | 41.695 Kg/h |
| MeOH | 91.5 | 94.85 | | 39.07 | | |
| CH$_4$ | 0.01 | 8 ppm | 16 ppm | | | |
| C$_2$+ | 0.16 | 4 ppm | 0.09 | | | |
| CO$_2$ | 0.29 | 28 ppm | 0.04 | | | |
| EtOH+ | 0.16 | 0.12 | | | 0.04 | |
| DME | 0.01 | 0.23 | 99.84 | 0.01 | | |
| MFOR | 0.02 | 23 ppm | | | | |
| TMA | 10 ppm | 1 ppm | | 3 ppm | | |
| H$_2$O | 7.85 | 4.8 | | 60.91 | 99.96 | |
| MEE | | | 0.03 | 75 ppm | | |

TABLE 2

| | Feed MeOH (81) | Reactor feed (93) | Purified DME product (132) | MeOH/H$_2$O Recycle (133) | H$_2$O Effluent | Steam consumption |
|---|---|---|---|---|---|---|
| Flow rate | 37.478 kg/h | 44.789 kg/h | 24.551 kg/h | 19.645 kg/h | 12.572 kg/h | 45376 Kg/h |
| Component | [wt %] | [wt %] | [wt %] | [wt %] | | |
| MeOH | 91.5 | 93.49 | | 38.75 | | |
| CH$_4$ | 0.01 | 7 ppm | 1 ppm | | | |
| C$_2$+ | 0.16 | 5 ppm | 0.03 | | | |
| CO$_2$ | 0.29 | 53 ppm | 15 ppm | | | |
| EtOH+ | 0.16 | 0.13 | | | 0.04 | |
| DME | 0.01 | 1.11 | 99.97 | 0.13 | | |
| MFOR | 0.02 | 26 ppm | | | | |
| TMA | 10 ppm | 1 ppm | | 4 ppm | | |
| H$_2$O | 7.85 | 5.26 | | 61.07 | 99.96 | |
| MEE | | | 26 ppm | 0.05 | | |

(All values in wt. % unless otherwise indicated)

The invention claimed is:

1. A process for the production of dimethylether (DME), said process comprising:
   a. dehydrating a methanol stream in the presence of a catalyst bed in a DME reactor system by passing the methanol stream over the catalyst to provide a first DME-containing product;
   b. reducing the first DME-containing product temperature and directly introducing the reduced temperture product into an olefin stripper column, stripping the reduced temperature product in said stripper column into two streams:
      i. an olefin stripper light fractions, and
      ii. a second DME-containing product;
      wherein sensible heat of the reduced temperature product provides energy for the olefin stripper column;
   c. introducing the second DME-containing product into a DME column, in which it is separated into:
      i. DME column overhead light fractions,
      ii. purified DME and
      iii. unreacted methanol and water bottoms fractions, and
   d. recycling the unreacted methanol and water bottoms fraction of step c.iii. to said DME reactor.

2. The process according to claim 1, wherein the olefin stripper light fractions is cooled and in a gas/liquid separator, separated in a gas fraction and a reflux liquid and the reflux liquid is used as reflux liquid in the olefin stripper.

3. The process according to claim 1, wherein one or more of the light fractions are separated into DME-containing off-gases, said off-gases are combined, washed with methanol to extract DME and the DME-containing methanol recycled to the methanol stream inputted to step a.

4. The process according to claim 1, wherein said methanol stream of step a. is obtained by passing a feed of crude methanol through a combined stabiliser/waste water column.

5. The process according to claim 1, wherein heat from step a is used to heat the combined stabiliser/waste water column.

* * * * *